United States Patent
Carlson et al.

(10) Patent No.: US 7,899,519 B2
(45) Date of Patent: Mar. 1, 2011

(54) EVALUATING A PATIENT CONDITION USING AUTONOMIC BALANCE INFORMATION IN IMPLATABLE CARDIAC DEVICES

(75) Inventors: Gerrard Merrill Carlson, Champlin, MN (US); Bruce H. Kenknight, Maple Grove, MN (US); Qingsheng Zhu, Wexford, PA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1040 days.

(21) Appl. No.: 11/168,614

(22) Filed: Jun. 28, 2005

(65) Prior Publication Data

US 2006/0293604 A1    Dec. 28, 2006

(51) Int. Cl.
*A61B 5/0402* (2006.01)
(52) U.S. Cl. ............................................ 600/509
(58) Field of Classification Search ............ 600/509, 600/519, 515, 529, 513, 483, 484
See application file for complete search history.

(56) References Cited

U.S. PATENT DOCUMENTS

| | | | | |
|---|---|---|---|---|
| 5,682,901 A | * | 11/1997 | Kamen | 600/519 |
| 5,891,044 A | * | 4/1999 | Golosarsky et al. | 600/509 |
| 5,902,250 A | * | 5/1999 | Verrier et al. | 600/515 |
| 6,126,595 A | * | 10/2000 | Amano et al. | 600/300 |
| 6,358,201 B1 | * | 3/2002 | Childre et al. | 600/300 |
| 6,480,733 B1 | * | 11/2002 | Turcott | 600/516 |
| 6,554,763 B1 | * | 4/2003 | Amano et al. | 600/26 |
| 2002/0128563 A1 | * | 9/2002 | Carlson et al. | 600/509 |
| 2002/0128564 A1 | * | 9/2002 | Carlson et al. | 600/509 |
| 2004/0176695 A1 | * | 9/2004 | Poezevara | 600/513 |
| 2005/0075553 A1 | * | 4/2005 | Sakai et al. | 600/372 |
| 2006/0111635 A1 | * | 5/2006 | Todros et al. | 600/484 |

* cited by examiner

*Primary Examiner*—Carl H. Layno
*Assistant Examiner*—Jon-Eric C. Morales
(74) *Attorney, Agent, or Firm*—Hollingsworth & Funk, LLC

(57) ABSTRACT

Systems and methods for evaluating a patient condition using autonomic balance information involve providing an implantable cardiac device that acquires a cardiac waveform from a patient. One or more characteristics associated with autonomic balance of the patient are detected and used to evaluate a patient condition, such as sleep onset, sleep stage, cardiac vulnerability over a predetermined duration, and sleep disordered breathing. Patient activity levels may be sensed and used to evaluate the patient's condition, such as for determining a level of systemic stress. Characteristics associated with the autonomic balance include calculating an LF/HF ratio waveform and/or determining one or more morphological features of the LF/HF ratio waveform. Coordination with a patient-external device may facilitate transmission of information about one or more of the cardiac waveform, the one or more characteristics associated with the autonomic balance, and a marked cardiac waveform.

19 Claims, 9 Drawing Sheets

EVALUATING A PATIENT CONDITION USING AUTONOMIC BALANCE INFORMATION IN IMPLATABLE CARDIAC DEVICES

FIELD OF THE INVENTION

The present invention relates generally to implantable cardiac methods and systems, and more particularly to systems and methods for evaluating a patient condition using autonomic balance information.

BACKGROUND OF THE INVENTION

The human body functions through a number of interdependent physiological systems controlled through various mechanical, electrical, and chemical processes. The metabolic state of the body is constantly changing. For example, as exercise level increases, the body consumes more oxygen and gives off more carbon dioxide. The cardiac and pulmonary systems maintain appropriate blood gas levels by making adjustments that bring more oxygen into the system and dispel more carbon dioxide. The cardiovascular system transports blood gases to and from the body tissues. The respiration system, through the breathing mechanism, performs the function of exchanging these gases with the external environment. Together, the cardiac and respiration systems form a larger anatomical and functional unit denoted the cardiopulmonary system.

The cardiopulmonary system is controlled by the sympathetic and parasympathetic nervous systems. Some organs receive innervation from both the sympathetic and parasympathetic nervous systems, and in some of these organs, the impulse discharge from this dual innervation exerts antagonistic effects, so that the amount of activity depends on the balance between the discharges over the two autonomic outflows. The balance between the sympathetic and parasympathetic nervous systems is denoted the autonomic balance.

The innervation of the natural pacemaker of the heart exhibits an antagonistic autonomic balance. The heart receives excitatory innervation from the sympathetic outflow of the upper four or five thoracic segments, which acts on the sinoatrial pacemaker node, the atrioventricular conduction system, the atrial and ventricular myocardium, and the coronary vessels. Excitation from this outflow accelerates the heart rate and increases the force of cardiac contraction.

The parasympathetic innervation originates from the medulla oblongata in the vicinity of the dorsal motor nucleus of the vagus and the nucleus ambiguous, and this influence is exerted on the sinoatrial and atrioventricular nodes and the atrial myocardium. Excitation from this output decelerates the heart rate. When the impulse discharge of the sympathetic system dominates, the heart rate accelerates, but when the parasympathetic system is dominant, the heart rate slows.

Autonomic imbalances have been implicated in a wide variety of pathologies, including depression, fatigue, premenstrual syndrome, hypertension, diabetes mellitus, ischemic heart disease, coronary heart disease and environmental sensitivity. Stress and emotional states have been shown to dramatically affect autonomic function.

Autonomic imbalances and other disorders may affect the cardiovascular, respiratory, and other physiological systems. For example, heart failure (HF) is a clinical syndrome that impacts a number of physiological processes. Heart failure is an abnormality of cardiac function that causes cardiac output to fall below a level adequate to meet the metabolic demand of peripheral tissues. Heart failure is usually referred to as congestive heart failure (CHF) due to the accompanying venous and pulmonary congestion. Congestive heart failure may have a variety of underlying causes, including ischemic heart disease (coronary artery disease), hypertension (high blood pressure), and diabetes, among others.

There are a number of diseases and disorders that primarily affect respiration, but also impact other physiological systems. Emphysema and chronic bronchitis are grouped together and are known as chronic obstructive pulmonary disease (COPD). Pulmonary system disease also includes tuberculosis, sarcoidosis, lung cancer, occupation-related lung disease, bacterial and viral infections, and other conditions.

Chronic obstructive pulmonary disease generally develops over many years, typically from exposure to cigarette smoke, pollution, or other irritants. Over time, the elasticity of the lung tissue is lost, and the lungs become distended, unable to expand and contract normally. As the disease progresses, breathing becomes labored, and the patient grows progressively weaker.

Disordered breathing is a respiratory system condition that affects a significant percentage of patients between 30 and 60 years. Disordered breathing, including apnea and hypopnea, may be caused, for example, by an obstructed airway, or by derangement of the signals from the brain controlling respiration. Sleep disordered breathing is particularly prevalent and is associated with excessive daytime sleepiness, systemic hypertension, increased risk of stroke, angina, and myocardial infarction. Disordered breathing can be particularly serious for patients concurrently suffering from cardiovascular deficiencies.

Various types of disordered respiration have been identified, including, apnea (interrupted breathing), hypopnea (shallow breathing), tachypnea (rapid breathing), hyperpnea (heavy breathing), and dyspnea (labored breathing). Combinations of the respiratory cycles described above may be observed, including, for example, periodic breathing and Cheyne-Stokes respiration (CSR). Cheyne-Stokes respiration is particularly prevalent among heart failure patients, and may contribute to the progression of heart failure.

SUMMARY OF THE INVENTION

The present invention relates generally to implantable cardiac methods and systems, and more particularly to systems and methods for evaluating a patient condition using autonomic balance information. Methods in accordance with the present invention involve providing an implantable cardiac device that acquires a cardiac waveform from a patient. One or more characteristics associated with autonomic balance of the patient are detected and used to evaluate a patient condition, such as, for example, sleep onset, sleep stage, cardiac vulnerability over a predetermined duration, and sleep disordered breathing.

Further embodiments involve sensing a patient activity level and evaluating the patient's condition using the sensed patient activity level, such as for determining a level of systemic stress. Characteristics associated with the autonomic balance include, for example, calculating an LF/HF ratio waveform and/or determining one or more morphological features of the LF/HF ratio waveform. Other embodiments involve coordinating with a patient-external device used for receiving information about one or more of the cardiac waveform, the one or more characteristics associated with the autonomic balance, and the marked cardiac waveform.

Devices in accordance with embodiments of the present invention include a housing configured for implantation in a patient. Electrodes are coupled to the housing and configured for sensing a cardiac waveform. A memory and a controller are provided in the housing. The controller is configured to detect one or more characteristics associated with an autonomic balance of the patient, and use the one or more autonomic balance characteristics to evaluate a patient condition.

Embodiments of devices in accordance with the present invention are configured to communicate with a patient-external device, wherein the controller and the patient-external device are coupled to respective communication devices to facilitate wireless communication between the patient-external device and the controller.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
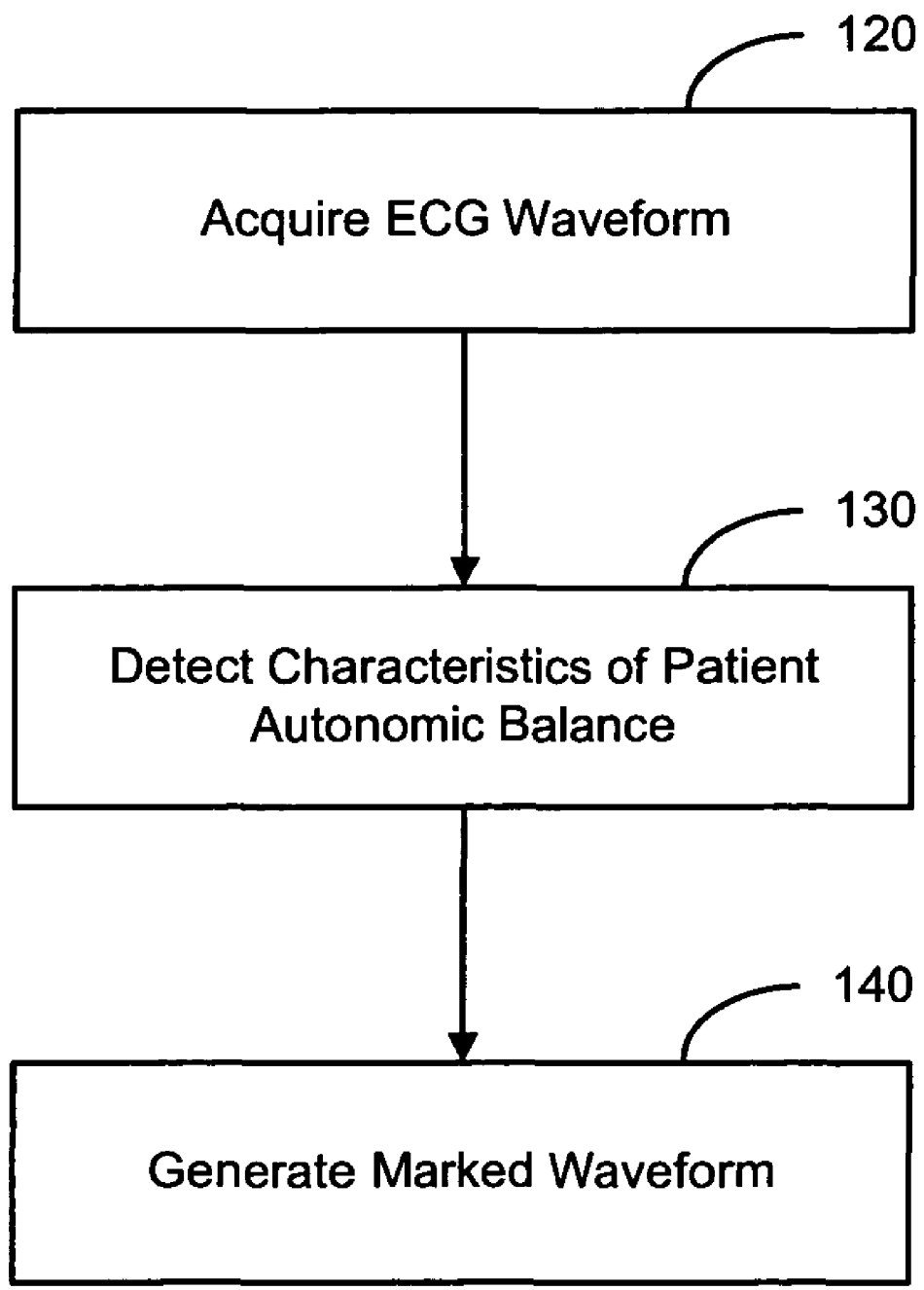
FIG. 1A is a flowchart of a method of characterizing patient respiration by generating a marked waveform in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings that form a part hereof, and in which are shown by way of illustration, various embodiments by which the invention may be practiced. It is to be understood that other embodiments may be utilized, and structural and functional changes may be made without departing from the scope of the present invention.

Assessment of a patient's condition is enhanced when an understanding the patient's neurohormonal component is combined with other cardiac and/or patient activity information. One measure of the patient's neurohormonal component used to determine autonomic balance may be determined using electrophysiology signals sensed by a patient-implantable medical device (PIMD). For example, an electrocardiogram (ECG) or electrogram (EGM) waveform describes the electrical activity of a patient's heart and may be used to determine autonomic balance, where typically ECG refers to waveforms sensed from surface electrodes and EGM refers to waveforms sensed patient-internally.

Autonomic balance may be determined by extracting R-wave to R-wave interval signals from EGM recordings. The signals may be decomposed to obtain the power spectral density of the signals, such as by using Fourier Transform techniques. Frequency ranges may be selected for analysis. For example, the low frequency (LF) signals may be designated as those within the range of about 0.04 to about 0.15 Hertz. High frequency (HF) signals may be designated as those within the range of about 0.15 to about 0.4 Hertz. A patients LF/HF ratio is determined by dividing the power of the LF signals by the power of the HF signals. The LF/HF ratio is a measure of autonomic balance.

Autonomic balance fluctuations during sleep may correspond to potential time windows of cardiac vulnerability. Bursts of sympathetic and vagal activity may signal otherwise hidden autonomic activity during sleep. Other fluctuations of autonomic balance may correspond to dream states, such as during REM sleep, with significant involvement from the heart and lungs.

Autonomic balance information, combined with cardiac information and patient activity information, may provide a more complete picture of systemic stress associated with physical activity. Higher levels of the LF/HF ratio combined with comparable levels of heart rate and patient activity may be an indicator of poor physical conditioning. Lower relative levels of sympathetic drive with comparable heart rate and activity level may indicate a patient in better condition.

Embodiments in accordance with the present invention are directed to using autonomic balance information in conjunction with cardiac parameters and/or patient activity level to assess the duration and nature of sleep and active periods of a patient. Knowledge of the patient's sleep, rest, or activity, state makes estimation of conditions at specific times possible. It is sometimes desirable to make measurements during sleep that are associated with re-optimization for heart failure therapies.

Use of the LF/HF ratio with heart rate and patient activity information may facilitate separation of time intervals that are most likely to correspond to sleep from the remainder of the day. The length, spacing, and frequency of such intervals associated with a heart-rate below a threshold, and activity level below a threshold, are important.

Additionally, shifts in the mean and standard deviations of the LF/HF ratio may be associated with a patient's state. Morphological features, such as the frequency of the peaks and valleys of the LF/HF ratio over a sliding window, may provide further insight into a patient's state of condition. The LF/HF ratio may be used to grade the level of systemic stress associated with conditioning during physical activity, as well as during periods of sleep, where the heart and lungs are significantly involved.

Further embodiments of the invention involve generating marked cardiac and/or respiration waveforms. The marked waveform may characterize a patient's normal respiration, autonomic balance, sleep identification, sleep state, sleep stage, disordered respiration episodes, or other events. For example, a marked waveform may include a time-based graph of the patient's autonomic balance, such as by graphing the LF/HF ratio. Impedance and/or EGM waveforms may include symbols indicating various characteristics based on sensor information coordinated with autonomic balance information.

If the patient's respiration is abnormal, the marked waveform may include symbols indicating respiration abnormalities or conditions affecting the respiration. For example, in the case of a disordered breathing episode, the marked respiration waveform may include symbols characterizing the severity, frequency, duration, and/or type of disordered breathing.

Additionally, or alternatively, the marked waveform may include symbols that provide information about one or more conditions affecting the patient's respiration, e.g., pollution index, sleep state, and/or posture. A marked waveform representing the autonomic balance of a patient suffering from a pulmonary disease, for example, may include symbols characterizing various parameters or other conditions associated with the disease, e.g., potential time windows of cardiac vulnerability.

The symbols used to mark the respiration waveform may comprise icons, graphics, alphanumeric characters, or other markers. The symbols may be positioned relative to the respiration waveform to indicate a time of occurrence of the particular parameter indicated by the symbol. A symbol may comprise a icon, graphic, numerical value and/or a textual descriptor associated with a characteristic, e.g., autonomic balance, cardiac vulnerability, sleep state, sleep stage, breathing disorder, etc.

FIG. 1A is a flow chart of a method of generating a marked waveform in accordance with embodiments of the invention. The method involves acquiring 120 an EGM waveform, and detecting 130 one or more characteristics associated with the patient's autonomic balance, such as by determining the LF/HF ratio. A waveform may be acquired by sensing a patient's EGM using electrodes that sense a patient's electrophysiology signals. The one or more characteristics associated with the patient's autonomic balance may comprise parameters associated with morphology of the LF/HF ratio, for example.

In various embodiments, the characteristics may further include conditions associated with the respiration, for example, using transthoracic impedance measurements along with the LF/HF ratio. Physiological conditions and/or contextual, non-physiological conditions may also be determined. Physiological conditions may include respiration characteristics, blood chemistry, expired $CO_2$, patient posture, activity, and/or other conditions. Contextual conditions may involve the ambient environment of the patient, such as ambient humidity, temperature, and/or pollution index, for example.

The respiration characteristics may include parameters of the respiration waveform morphology, including expiration and inspiration slope. The respiration characteristics may include characteristics of the respiration derived from the respiration waveform, e.g., respiration rate, tidal volume, minute ventilation, and breath intervals. Additionally or alternatively, the respiration characteristics may involve symptoms or physiological conditions that may be derived or detected from the LF/HF ratio and respiration waveform, e.g., pulmonary congestion, or disordered breathing episodes. The respiration characteristics may also include parameters characterizing respiration abnormalities, such as the duration, severity, frequency, and/or type of disordered breathing.

The acquired EGM waveform and the detected characteristics of patient respiration may be used to generate 140 a marked waveform. The marked waveform may include, for example, the acquired EGM waveform and one or more symbols or other indicators representative of the characteristics. In one implementation, the symbols may be used to indicate discrete portions of the EGM waveform corresponding to the occurrence of the characteristics. In another implementation, the symbols may indicate general conditions or characteristics that pertain globally to a continuous portion the EGM waveform. Various information, including the acquired EGM waveform, information associated with the characteristics, and/or the marked waveform may be stored in memory, transmitted to a separate device, displayed on a computer screen or other type of display, and/or printed for example.

In one implementation, the system for generating a marked waveform may be implantable or include an implantable component. An implantable system for generating a marked waveform may be implemented, for example, as a component of a cardiac device such as a pacemaker, defibrillator, cardiac resynchronizer, implantable cardiac monitor, or other implantable cardiac device. Devices and methods that provide marked waveforms and characterize patient sleep states are further described in commonly owned U.S. patent application Ser. No. 10/824,941 filed Apr. 15, 2004; and U.S. patent application Ser. No. 10/920,675 filed on Aug. 17, 2004, which are hereby incorporated herein by reference.

In another example, the system for generating the marked waveform may be implemented using both patient-internal and patient-external devices operating in coordination. In this example, a first set of components of a marked waveform system may be implemented in one or more patient-internal devices and a second set of components of the marked waveform system may be implemented in one or more patient-external devices. In various configurations, the patient-internal and patient-external devices may communicate through wired or wireless communication links to accomplish marked waveform generation.

Sleep and its various states have been linked to an increase in respiratory and cardiac disorders, particularly for patients with cardiopulmonary disorders. For example, some epidemiologic studies note a peak incidence of sudden cardiac death around 5 to 6 am. One explanation for this peak suggests an association between the incidence of sudden death and episodes of rapid eye movement (REM) sleep, morning wakening or arousal. The mechanism eliciting fatal arrhythmia may be related to the autonomic balance of the cardiovascular system during the REM state or morning wakening.

Non-REM sleep may also be linked to an increased likelihood of cardiac arrhythmia. Some patients are predisposed to nocturnal cardiac paroxysms associated with surges in vagal activity, indicative of autonomic imbalance. Because non-REM sleep is associated with conditions of "vagal dominance," characterized by lower heart rate and low-to-high frequency power ratios, autonomic imbalance may be implicated in these nocturnal arrhythmias.

Sleep may also be associated with increased respiratory disruptions. A significant percentage of patients between the ages of 30 and 60 experience some symptoms of disordered breathing, generally occurring during sleep. Sleep apnea is a particularly serious form of sleep-disordered breathing in which the patient may cease to breathe for periods of time. Obstructive apnea occurs when the patient's airway is obstructed by the collapse of soft tissue into the respiratory passage. Central sleep apnea is caused by a derangement of the central nervous system control of respiration. Patients suffering from central sleep apnea cease to breathe when control signals from the brain to the respiratory muscles are absent or interrupted.

Regardless of the type of sleep apnea, people experiencing an apnea event stop breathing for a period of time. The cessation of breathing may occur repeatedly during sleep, sometimes hundreds of times a night and sometimes for a minute or longer. Disordered breathing is associated with excessive daytime sleepiness, systemic hypertension, increased risk of stroke, angina and myocardial infarction. Respiratory disruption caused by sleep apnea and other disordered breathing episodes can be particularly serious for patients concurrently suffering from cardiovascular deficiencies, such as congestive heart failure.

Variations in disease, medication, etiology, and phenotype may all contribute to a patient's sleep state propensities to cardiac or respiratory disorders. Sleep state classification may be used to provide more effective therapy, better diagnostic information, and improved prognostic and preventive therapy capabilities. Using autonomic balance information for sleep state classification in concert with therapy may result in improved therapy management for both cardiac and respiratory conditions, such as those described above. Tracking autonomic balance during sleep states may also provide a mechanism for improved diagnosis of sleep-related disorders.

Diagnostic testing or therapeutic device testing may be advantageously performed during sleep or during particular sleep states. Diagnostic testing may involve, for example, assessing the patient's autonomic integrity during sleep and the possible use of REM episodes as a surrogate for stress testing. Performing diagnostic procedures during sleep recognizes opportunities afforded by sleep or particular sleep states to routinely perturb the cardiovascular system under controlled conditions to assess the patient's autonomic response.

Therapeutic device testing, such as AVI search, capture threshold, and cardiac template acquisition, may also be performed during sleep. Sleep provides a period of time to perform such therapeutic device tests while the patient's activity is low, resulting in more effective and consistent testing conditions. Various embodiments of the invention involve sensing a physiological condition associated with autonomic balance and using the condition to classify the patient's sleep state and/or cardiac vulnerability.

Sensing a condition associated with the LF/HF ratio may be used to discern periods of cardiac vulnerability. Sleep state classification may be further enhanced by detecting a condition associated with the autonomic balance of the patient, the condition associated with the quality of the patient's sleep.

According to embodiments of the invention, a sleep state classification approach involves sensing autonomic balance using a ratio of LF/HF, enhancing assessment of a patient's condition by measuring the neurohormonal component that determines the quality of the patient's sleep. Imbalances and/or changes in the neurohormonal component may correspond to potential time windows of cardiac vulnerability.

Discriminating between periods of sleep and periods of wakefulness may be accomplished, for example, by sensing patient activity. According to this approach, if the patient's activity level is relatively low, e.g., below a sleep threshold, then the patient is determined to be asleep. The level of patient activity may be detected using an accelerometer, heart rate sensor, respiratory minute ventilation (MV) sensor or other types of sensors, for example.

Information derived from the autonomic balance may be used in combination with information related to the patient's activity. This technique may be used to determine, for example, sleep onset and sleep offset, the duration and degree of arousals from sleep, and to classify sleep states.

In accordance with embodiments of the invention, a sleep state classification processor receives the outputs of the one or more sensors configured to sense signals associated with autonomic balance and patient activity. The sleep state processor may perform sleep state classification on a real-time basis, or may process previously acquired and stored sensor data in a batch mode to retrospectively classify the sleep states of one or more sleep periods, as well as to determine potential time windows of cardiac vulnerability.

Sleep state classification may involve an adaptive approach, wherein the sleep state processor learns the physiological responses of a patient in various sleep states. The learned responses may be used to enhance the accuracy and/or sensitivity of the sleep state classification. Adaptive sleep state classification may involve monitoring the changes in one or more physiological signals over a period of time and adjusting thresholds used for determining sleep onset, sleep offset, and various sleep states to accommodate the drift or other changes in the sleep-related signals.

In one configuration, one or more of the sensors used to detect the sleep-related conditions, e.g., the autonomic balance and/or the condition associated with the patient's activity, may be implantable, or may utilize an implantable component. In another configuration, the sleep state processor may be partially or fully implantable. In other configurations, both the sensors and the sleep state processor may be implantable or use implantable components.

As previously discussed, sleep state classification may be useful in coordinating sleep state informed therapy delivery to treat various disorders and to perform sleep state informed testing and monitoring. In one example implementation, cardiac therapy may be triggered during particular sleep states to reduce the likelihood of cardiac arrhythmia during vulnerable sleep periods. In a similar manner, sleep state classification may be used to trigger disordered breathing therapy to preclude or reduce episodes of sleep-disordered breathing.

Figure 1B:
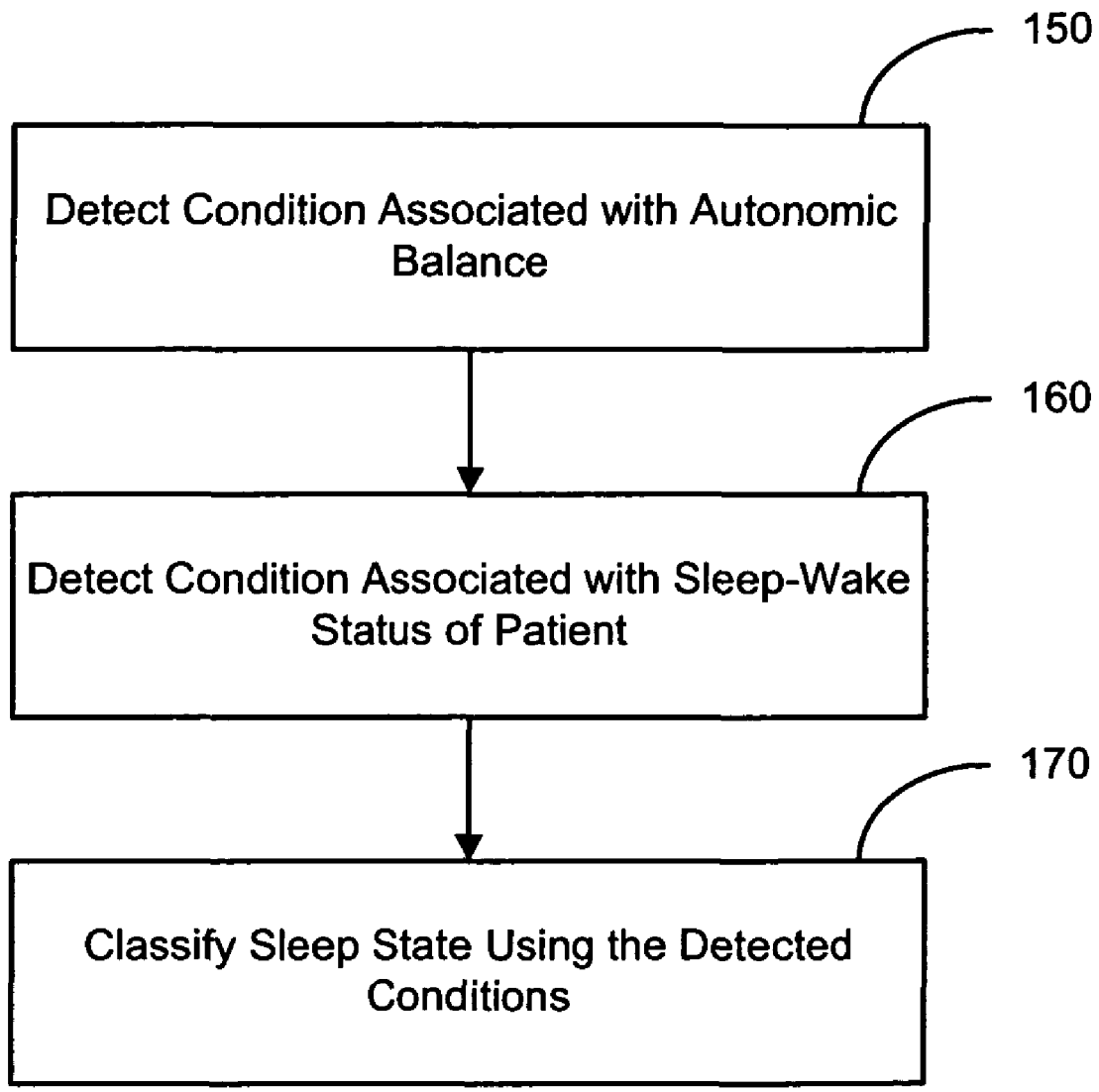
FIG. 1B is a flow graph of a method of sleep state classification involving at least one condition associated with autonomic balance and at least one condition associated with a sleep-wake status of a patient in accordance with embodiments of the invention.

The flow graph of FIG. 1B depicts a method of classifying sleep states according to embodiments of the invention. Autonomic balance is detected 150 and is used in conjunction with a detected condition 160 of a patient's sleep-wake status to classify 170 the patient's sleep state. Classifying 170 the one or more sleep states is performed at least in part implantably. Using the detected 150 autonomic balance, the system may determine that the patient is in a period of cardiac vulnerability.

Figure 2:
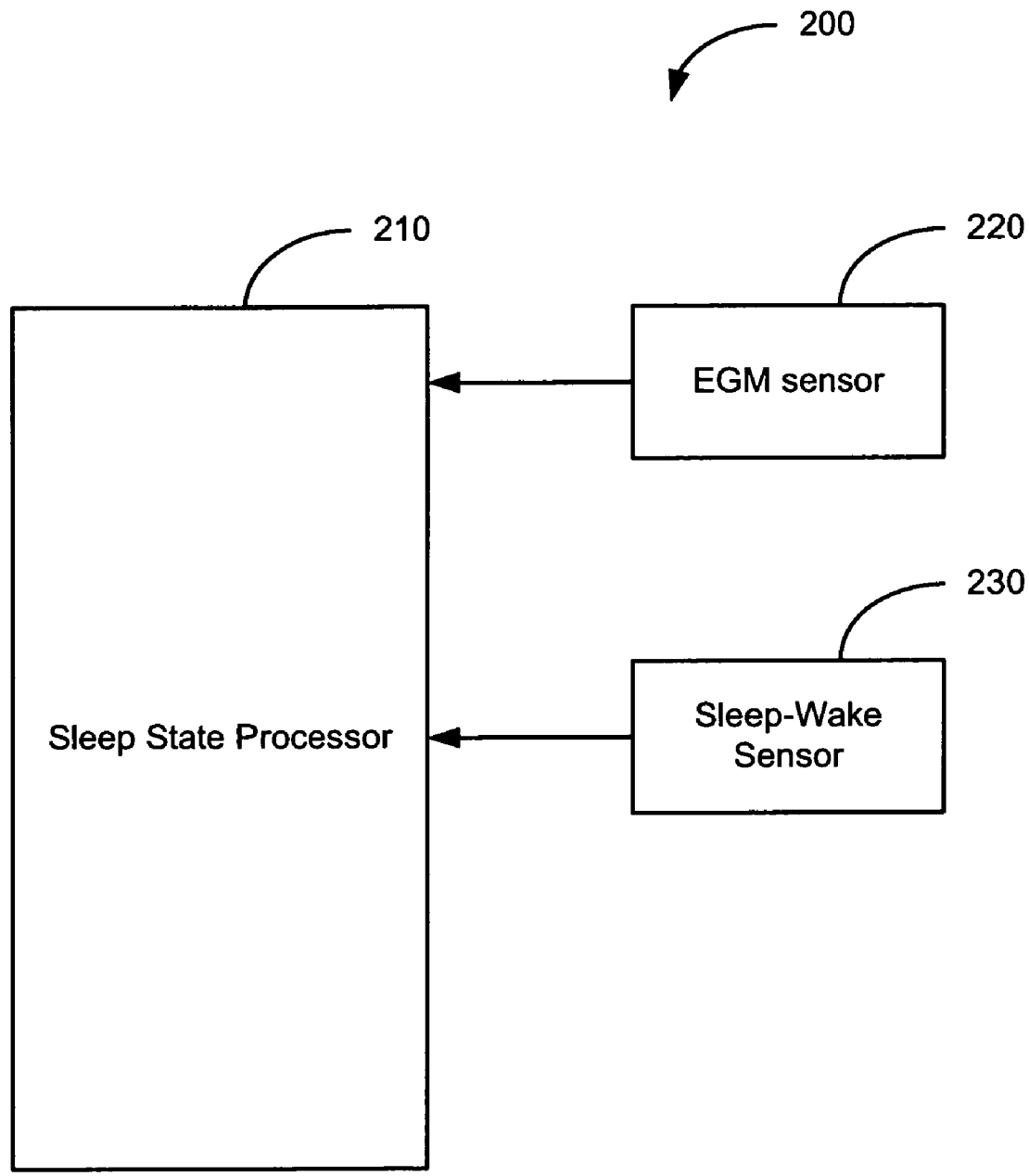
FIG. 2 is block diagram of system suitable for implementing a sleep state classification method in accordance with embodiments of the invention.

A block diagram of a system 200 suitable for implementing a sleep state classification method according to embodiments of the invention is illustrated in FIG. 2. The sleep state classification system 200 may include one or more sensors 230 used to sense patient activity as well as EGM sensors 220 configured to detect autonomic balance information. In one example implementation, the sensor 230 may be responsive to patient activity. When the patient's activity falls below a threshold, the patient is considered to be asleep. When the patient's activity rises above the activity threshold, the patient is considered to be awake. Other methods of detecting whether the patient is asleep or awake are also possible.

The sensor 230, and any additional sensors, are coupled to a sleep state processor 210 that detects and processes the sensor outputs. The sleep state processor 210 may use outputs from the sensor 230 and the EGM sensor 220 to determine if the patient is awake or asleep, to determine the duration and degree of arousals from sleep, to classify sleep states using autonomic balance information, to determine periods of cardiac vulnerability, and to determine the duration of various sleep states, for example.

In one embodiment, one or both the sensor 230 and the EGM sensor 220 are positioned external to the patient and the sleep state processor 210 is implantable or includes an implantable component. In another embodiment, one or both the sensor 230 and the EGM sensor 220 are fully or partially implantable and the sleep state processor 210 is positioned externally to the patient. In yet another embodiment, the sensor 230, EGM sensor 220, and the sleep state processor 210 all include implantable components or are fully implantable.

Components of the sleep state classification system 200 may employ wireless communications. For examples, the sensor 230 and EGM sensor 220 may be coupled to the sleep state processor 210 using a wireless communications link. In one example, some or all of the sensors 220, 230 use remote communication capabilities, such as a wireless proprietary or a wireless Bluetooth communications link.

The sleep state processor 210 may adaptively classify sleep states by learning patient responses in connection with various sleep states. In one example, the sleep state processor 210 may perform sleep state classification by comparing sensor signal levels and computed autonomic balance levels to predetermined thresholds. Initial thresholds may be established using clinical data derived from a group of individuals, or using patient-specific data. After initial thresholds have been established, the sleep state processor 210 may update the thresholds to provide more sensitive and/or more accurate sleep state classification based on data acquired from the patient over time. A sleep state threshold may be updated by a recent history of the sensor output level associated with a particular sleep state. This process may involve collecting data over time to determine the sleep patterns of the patient and adjusting the thresholds based on the sleep patterns. By this process, initially established thresholds, e.g., sleep onset threshold for an accelerometer output, or autonomic balance threshold for an EGM sensor output, may be modified as additional data is acquired from the patient regarding the relationship between the sensor output levels and patient's sleep state.

Figure 3:
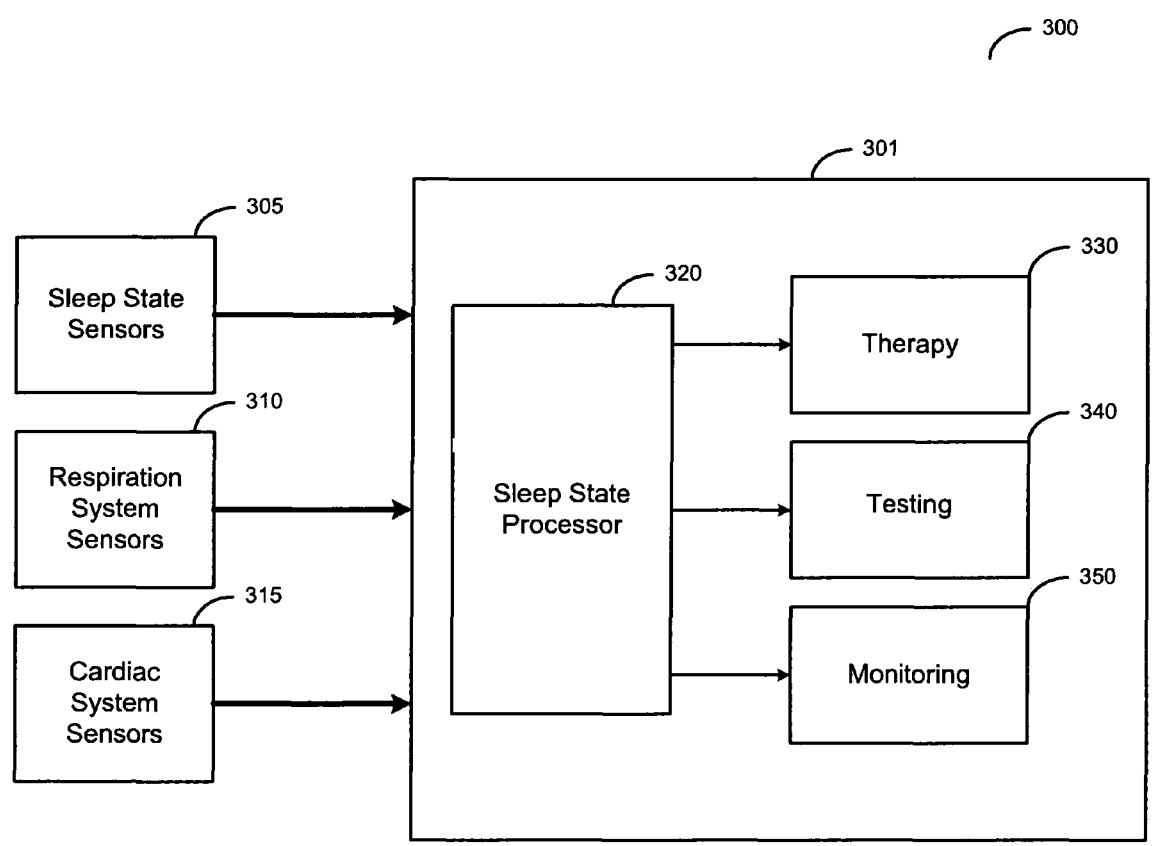
FIG. 3 is a block diagram of a medical device utilizing a sleep state classification system using autonomic balance information implemented in accordance with embodiments of the invention.

FIG. 3 presents a block diagram illustrating a medical system 300 utilizing a neurohormonal activity and sleep state classification system implemented in accordance with embodiments of the invention. Such a medical system 300 may be employed, for example, to perform sleep state informed diagnostic monitoring and/or diagnostic testing to assess the capabilities of the patient's physiological systems. Such diagnostic monitoring or testing may involve one or more physiological systems, including, for example, the cardiac and respiratory systems. Additionally, or alternatively, the medical system 300 may be used to provide sleep state informed therapy to a patient, for example, cardiac rhythm therapy, respiratory therapy, or other types of therapy enhanced using neurohormonal activity information and sleep state classification. Further, the medical system 300 may be used to perform sleep state informed therapeutic device testing. Such a medical system 300 may be purely or predominantly diagnostic in function, purely or predominantly therapeutic in function, or may perform a combination of therapeutic and diagnostic operations.

The medical system 300 includes a medical device 301 coupled to a variety of sensors 305, 310, 315. The sensors 305, 310, 315 provide physiological information used in connection with neurohormonal activity and sleep state classification and the therapeutic and/or diagnostic operations performed by the medical device 301. Sleep state sensors 305, including one or more sensors indicative of the sleep-wake status of the patient, e.g., a patient activity sensor, may be used. Sleep state may also be determined using autonomic balance information from cardiac sensors 315.

The medical device 301 may also be coupled to sensors 310, 315 configured to detect one or more aspects of the patient's physiological systems, including, for example, the cardiac and/or respiratory functions of a patient. In various configurations, the medical system 300 may monitor, test, or provide therapy to the patient, including cardiac and/or respiratory therapy. Cardiac sensors 315, e.g., cardiac electrodes, may be used to sense the electrical activity of the heart. The cardiac system sensors may comprise patient-internal or patient-external cardiac electrodes electrically coupled to the patient's heart tissue, for example. The cardiac sensors 315 may be used to detect autonomic balance, providing sleep state information in addition to typical cardiac information to the medical device 301.

The medical device 301 may be coupled to one or more respiratory system sensors 310 capable of detecting conditions associated with the respiratory functions of the patient. In one embodiment, the respiratory functions of the patient may be monitored using a transthoracic impedance sensor. Transthoracic impedance tracks the patient's respiratory effort, increasing upon respiratory inspiration and decreasing upon respiratory expiration. The transthoracic impedance signal may be used to determine the patient's respiration tidal volume (TV), minute ventilation (MV), and/or other respiratory parameters, for example. Sensors other than, or in addition to, the cardiac and respiration system sensors described herein may be used to detect cardiac and/or respiration functions of the patient.

The sleep state processor 320 uses information from the sleep state sensors 305 and/or cardiac sensors 315 to determine the states of the patient's sleep, including, for example, sleep onset and termination. Information generated by the sleep state processor 320 may be used by other components of the medical device 301 to provide therapy, testing, and/or monitoring coordinated with the patient's sleep state.

Sleep state information may be provided to a therapy module 330 coupled to the sleep state processor 320. The therapy module 330 controls the delivery of sleep state informed therapy to the patient. For example, cardiac therapy may be coordinated using sleep state classification information to provide cardiac arrhythmia therapy during periods of cardiac vulnerability. Sleep state classification may also be used, for example, in connection with delivery of sleep informed therapy to preclude or reduce episodes of disordered breathing while the patient is asleep. Other types of therapy may also be enhanced using neurohormonal activity information and sleep state classification.

The sleep state processor 320 may be coupled to a monitoring unit 350 configured to collect and store historical data acquired from the sleep state sensors 305, respiratory system sensors 310, the cardiac system sensors 315, and/or other components of the medical device 301. The monitoring unit 350 may track one or more patient conditions and provide data used in the analysis of various physiological processes. The monitoring module 350 may collect data useful in assessing trends of various physiological systems. Trending data may be used to identify gradual changes in the patient's physiological conditions, especially those altered by sleep and/or neurohormonal activity, or by particular sleep states.

A testing module 340 may be implemented within the medical device 301 to control diagnostic tests and/or to control device testing to maintain or improve the operation of the medical device 301. Information from the sleep state processor 320 is used by the testing module 340 to ensure that diagnostic and/or device testing appropriately coincides with a sleep or waking state of the patient, or to a particular state of sleep.

Diagnostic testing may be employed to investigate the functioning of one or more of the patient's physiological systems. Diagnostic testing may include changing one or more parameters of the patient's therapy, e.g., cardiac rhythm therapy, and assessing the impact of the change on the patient. For example, the patient's therapy regime may be altered during sleep, or during a particular sleep state, to determine the effect of the change on the patient.

A diagnostic testing methodology may use neurohormonal activity and sleep state classification to determine the general behavior of the patient's physiological responses in connection with various sleep states. Such a process may involve determining the patient's intrinsic responses to normal variations in physiologic processes. In addition, the patient's evoked physiological responses to device-based stimuli may also be determined.

Various methods of sleep onset and sleep offset detection may be used in connection with the neurohormonal activity and sleep state classification approaches of the present invention. Methods and systems related to sleep detection are further described in commonly owned U.S. patent application entitled "Sleep Detection Using an Adjustable Threshold," identified by Ser. No. 10/309,771, filed on Dec. 4, 2002, and incorporated by reference herein in its entirety.

Figure 4A:
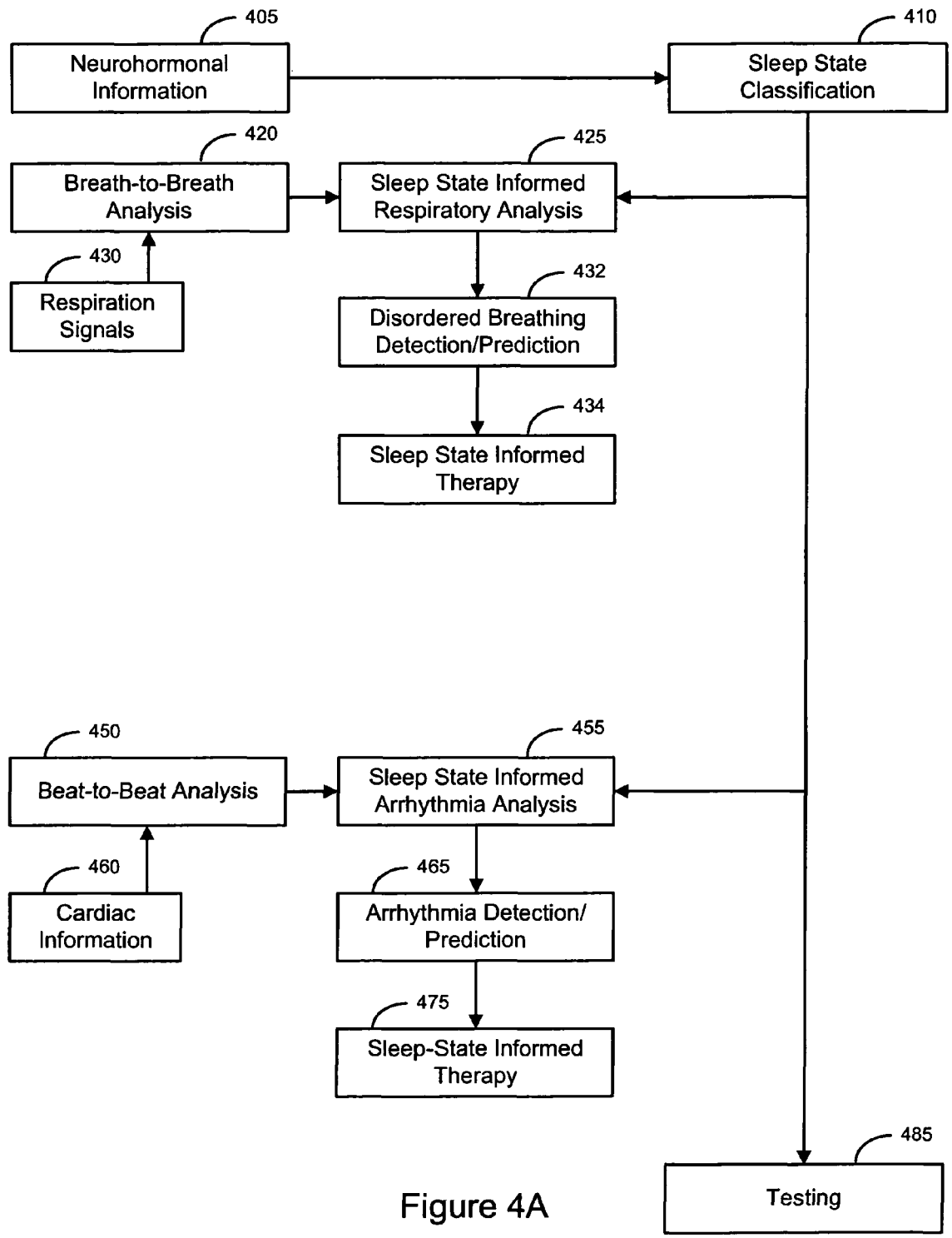
FIG. 4A is a process flow diagram illustrating sleep state determination in cooperation with therapy delivery and testing using autonomic balance information in accordance with embodiments of the invention.

FIG. 4A is a process flow diagram illustrating a process for using neurohormonal activity and sleep state classification in cooperation with therapy delivery and testing in accordance with embodiments of the invention. As presented in the process flow diagram of FIG. 4A, the system detects 460 cardiac signals and analyzes 450 the cardiac signals on a beat-to-beat basis. Beat-to-beat cardiac signal analysis 450 may be used to perform arrhythmia detection 465 based on rate and/or morphological analysis techniques, for example. Depending on the type of arrhythmia detected, if any, an appropriate therapy 475 may be delivered to the heart. In one implementation, bradycardia pacing therapy may be delivered to the heart to maintain the patient's rhythm at a hemodynamically sufficient rate. In other examples, a variety of tiered tachyarrhythmia therapies, including, for example, anti-tachycardia pacing, cardioversion, and/or defibrillation may be available to treat detected cardiac tachyarrhythmias.

The illustrative system utilizes neurohormonal information 405 for sleep state classification 410. Neurohormonal information 405 and sleep state classification 410 may be used in cooperation with the beat-to-beat cardiac signal analysis 450 to implement sleep state informed arrhythmia analysis 455, thus augmenting the delivery of cardiac arrhythmia therapy 475. In one example, bradycardia pacing therapy may be enhanced by the ability to switch to a lower pacing rate when the patient is determined to be asleep and relaxed. Such a procedure may be advantageous, for example, both to increase the device lifetime and to reduce stress on the heart. In a further example, preventive arrhythmia therapy 475 may be delivered during sleep or based on prediction of future arrhythmic events, e.g., upon detection of a pro-arrhythmic sleep state 465 or stress detected using neurohormonal information 405. In one example, preventive arrhythmia therapy may be delivered to prevent tachyarrhymias known to occur more frequently during periods of cardiac vulnerability or during arousal from sleep.

Neurohormonal activity and sleep state classification may also be used in connection with therapy to terminate or prevent sleep-disordered breathing. Various therapies may be implemented to treat sleep-disordered breathing, including maintaining continuous positive air pressure to prevent collapse of tissue into the respiratory passage, electrical stimulation of nerves or muscles, and cardiac pacing therapy, for example. Because disordered breathing is more likely to occur when the patient is asleep, disordered breathing detection or prediction 432 may be augmented by employing sleep state informed respiratory analysis 425 in accordance with embodiments of the present invention.

Detection of disordered breathing may be accomplished by detecting 430 respiration signals representing the patient's breathing cycles and analyzing each breath 420. In one implementation, disordered breathing, including, e.g., hypopnea and apnea, may be detected 432 by monitoring the respiratory waveform output produced by a transthoracic impedance sensor.

When the tidal volume (TV) of the patient's respiration, as indicated by the transthoracic impedance signal, falls below a hypopnea threshold, then a hypopnea event is declared. For example, a hypopnea event may be declared if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

Another method of detecting 432 disordered breathing involves analyzing the patient's respiratory patterns. According to this method, the patient's respiratory cycle is divided into several periods, including, inspiration, expiration, and non-breathing periods. The inspiration, expiration, and non-breathing respiratory periods are analyzed for patterns consistent with various types of disordered breathing. Methods and systems for detecting disordered breathing based on respiration cycle patterns are more fully described in commonly owned U.S. patent application entitled "Detection of Disordered Breathing," identified by Ser. No. 10/309,770, filed Dec. 4, 2002, and incorporated herein by reference.

Methods and systems for predicting disordered breathing are described in commonly owned U.S. patent application Ser. No. 10/643,016, filed Aug. 18, 2003, entitled "Prediction of Disordered Breathing," which is hereby incorporated herein by reference. As described in the above-referenced patent application, sleep-disordered breathing may be predicted based on a number of patient conditions that increase the likelihood of disordered breathing. Conditions that predispose the patient to disordered breathing include, for example, air pollution, alcohol use, and pulmonary congestion, among other conditions. In addition to predisposing conditions that make disordered breathing more likely, various precursor conditions may be used to determine that a disordered breathing episode is imminent. For example, blood chemistry, hyperventilation, and the regular periodicity of previous disordered breathing episodes may be used to predict an imminent onset of disordered breathing.

If disordered breathing is detected or predicted 432, an appropriate therapy 434 may be provided to terminate or prevent the disordered breathing. Disordered breathing therapy 434 may include, for example, cardiac pacing, nerve stimulation, or other types of disordered breathing therapy, such as those previously discussed.

Neurohormonal information 405 and sleep state classification 410 may also be used to identify preferable periods of time for performing 485 various testing procedures, including, for example, diagnostic testing and/or testing of therapeutic device parameters. In various implementations, sleep state informed diagnostic testing may allow testing to assess the patient's autonomic integrity.

Sleep state classification also provides an opportunity to test one or more parameters of a therapeutic device while the patient's activity is low. Such testing may involve, for example, capture threshold testing for a cardiac pacing device and cardiac signal morphology template acquisition to be used in connection with cardiac arrhythmia detection. Thus, neurohormonal activity and sleep state classification may be used to provide more effective therapy, better diagnostic information, and improved prognostic and predictive capabilities.

Figure 4B:
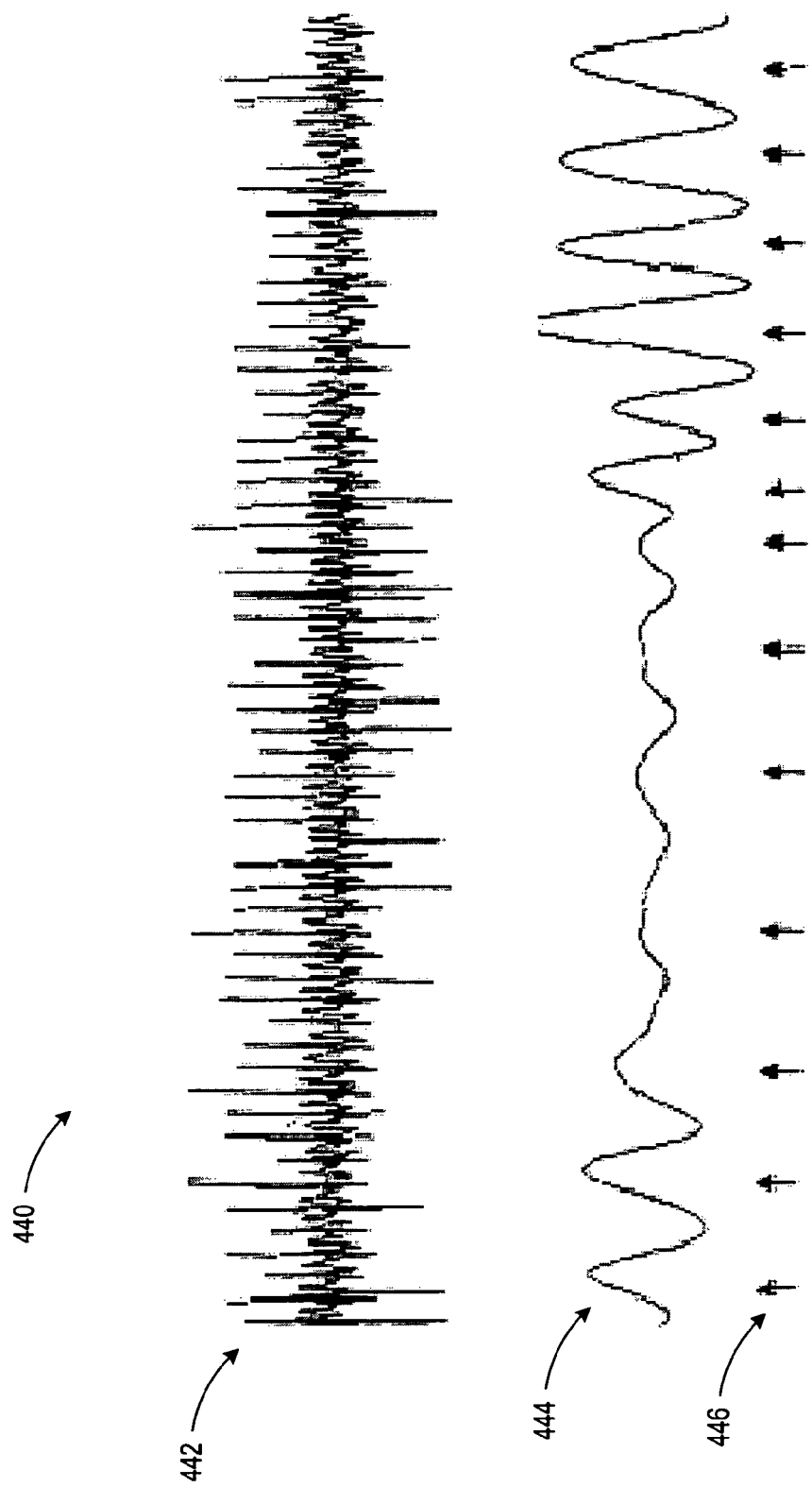
FIG. 4B illustrates a marked respiration waveform including respiration and ECG graphs in accordance with embodiments of the invention.

FIG. 4B illustrates a graph 440 of a respiration waveform 444 and an EGM waveform 442, including marking symbols 446 in accordance with embodiments of the invention. In this example, the respiration waveform 444 and EGM 442 were produced by a medical device having a transthoracic impedance sensor and intracardiac EGM electrodes, however, autonomic balance information may be acquired for waveform marking without the use of breathing sensors, as described above.

In addition to displaying the respiration waveform 440, the graph 440 may show other measurements and/or other waveforms. In FIG. 4B, the EGM waveform 442 is shown above the respiratory waveform 444. The EGM waveform 442 is time-aligned with respiration waveform 444, and can be marked with indicators corresponding to autonomic balance information, such as the marking symbols 446 illustrated as arrows in the graph 440. Displaying marked EGM and/or respiration waveforms and other waveforms related to patient conditions allows the patient's physician to verify, for example, one or more characteristics associated with the autonomic balance of the patient, and/or to verify periods of patient vulnerability. This confirmation may be used to guide diagnostics and/or therapy. Symbols annotating autonomic balance information provide further diagnostic information for physicians.

Figure 5:
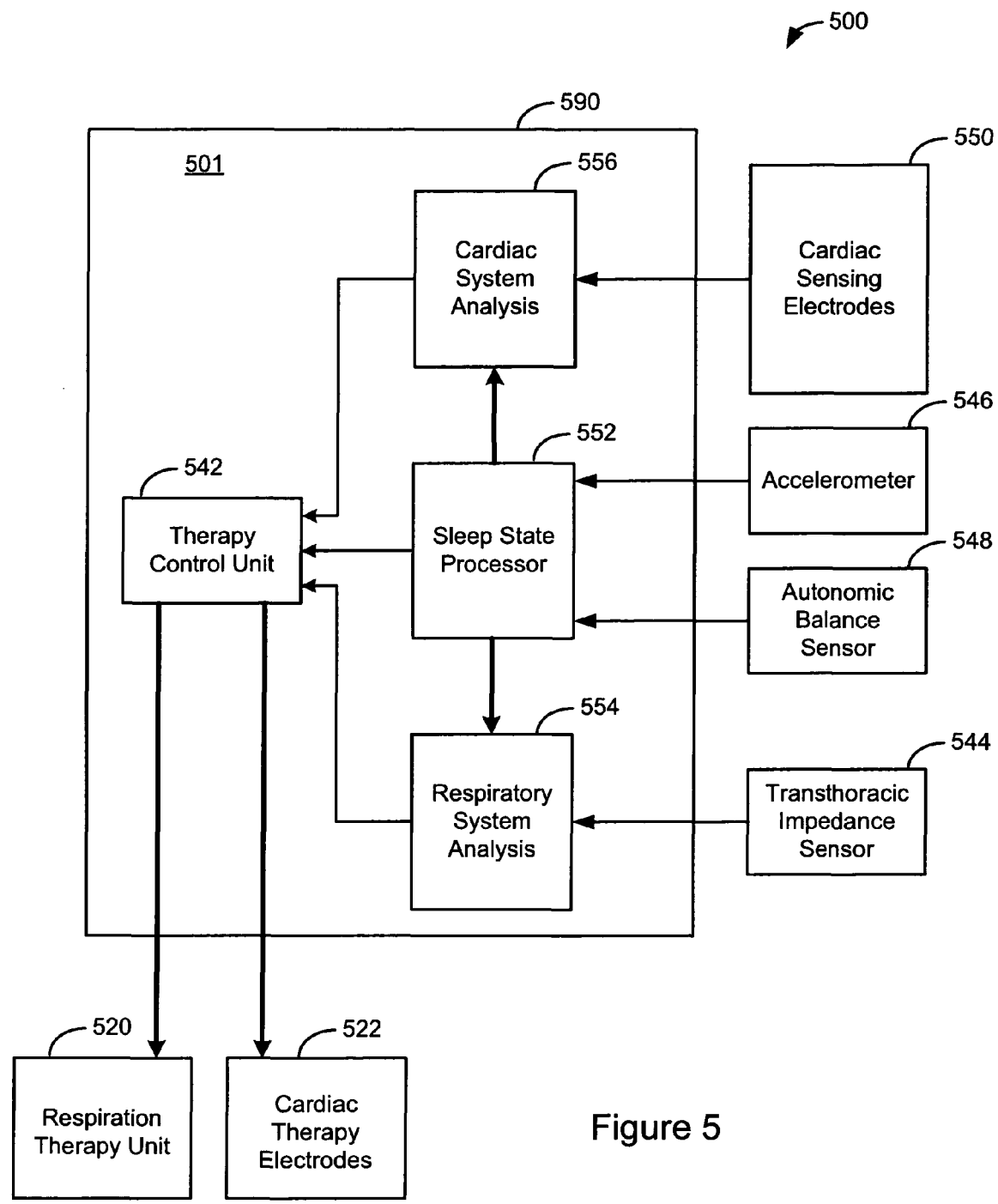
FIG. 5 is a block diagram of a medical device that may be used to perform sleep state informed therapy using autonomic balance information in accordance with embodiments of the invention.
Figure 6:
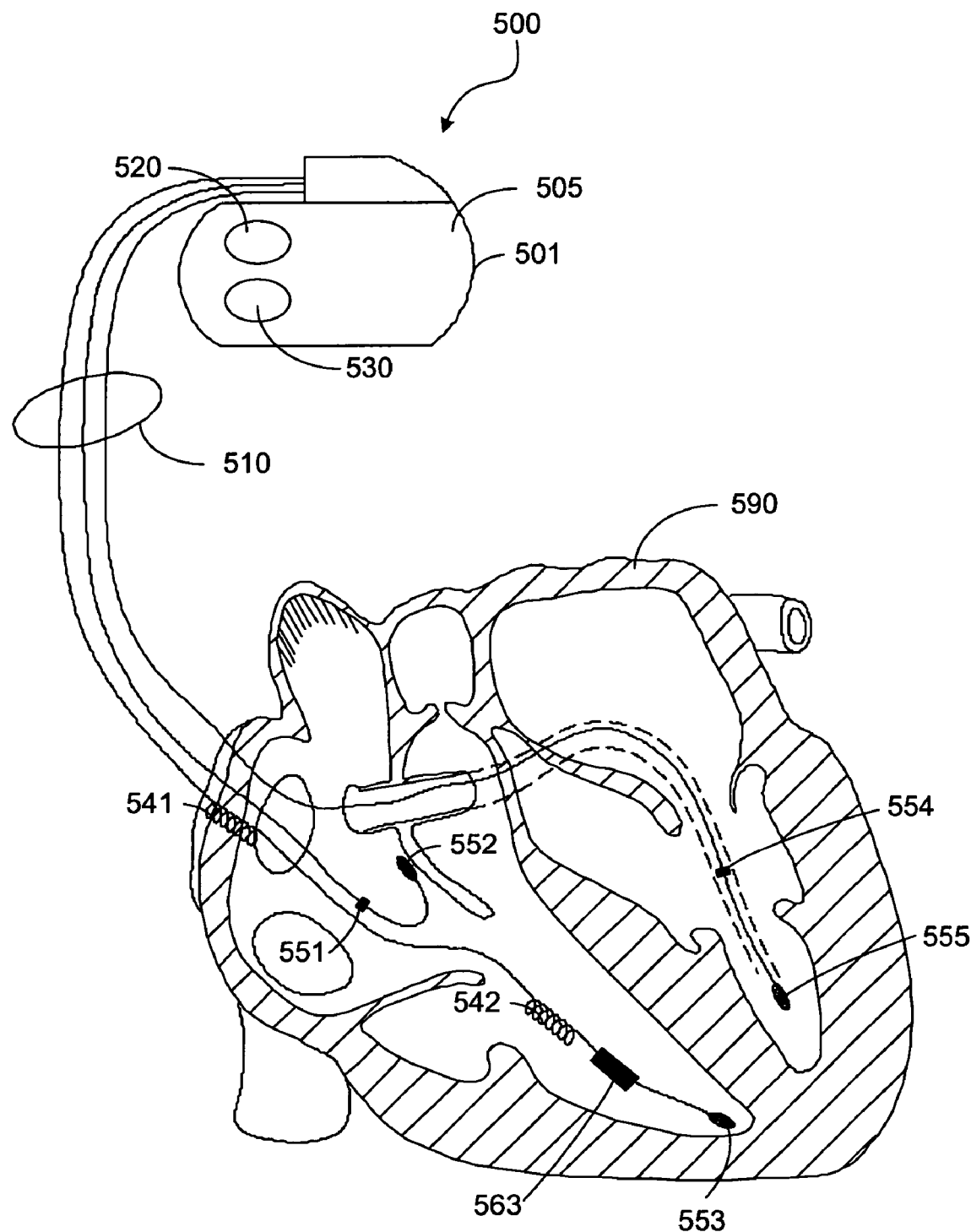
FIG. 6 is an illustration of an implantable cardiac device using autonomic balance information, including a lead assembly shown implanted in a sectional view of a heart, in accordance with embodiments of the invention.

FIGS. 5 and 6 illustrate a medical system that may be used to perform sleep state and neurohormonal informed therapy in accordance with embodiments of the invention. The block diagram of FIG. 5 shows the medical system 500 divided into functional blocks. It will be appreciated by those skilled in the art that there exist many possible configurations in which these functional blocks can be arranged and implemented. The example depicted in FIG. 5 is one possible functional arrangement.

FIG. 5 illustrates an implantable cardiac pulse generator 501 enclosed in a housing 590 and configured to provide therapy for cardiac arrhythmia. Various cardiac rhythm therapies, including bradycardia pacing, anti-tachycardia pacing, defibrillation, and cardioversion, may be implemented in cooperation with neurohormonal activity and sleep state classification in accordance with embodiments of the invention.

Optionally, the medical device 500 may also be configured to detect respiratory disorders, e.g., sleep-disordered breathing, and to provide therapy to mitigate the respiratory disorders. Disordered breathing therapy, including cardiac pacing and/or other types of disordered breathing therapy, such as continuous positive air pressure (CPAP), nerve stimulation, muscle stimulation or other therapy for treating disordered breathing, may be controlled or provided by components of the cardiac pulse generator 501.

Although FIG. 5 depicts an autonomic balance and sleep state classification system implemented in a cardiac pulse generator 501, it is understood that configurations, features, and combinations of features described in the disclosure may be implemented in a number of medical devices. Neurohormonal activity and sleep state classification may be implemented in connection with various diagnostic and therapeutic devices and such embodiments and features are not limited to the particular devices described herein.

Further, although various embodiments involve devices or systems having an implantable control system and implantable sensors, it is understood that therapy or diagnostic systems utilizing the neurohormonal activity and sleep state classification methodologies of the present invention may be configured so that the control system or components of the control system are arranged externally to the patient. The sensors and the control system, and in particular the patient neurohormonal activity and sleep state classification system, may involve patient-external components, patient-internal components or a combination of patient-external and patient-internal components.

In the embodiment illustrated in FIG. 5, the implantable pulse generator 501 includes circuitry for providing cardiac rhythm therapy 542 to treat various arrhythmic conditions. Cardiac arrhythmia therapy is implemented by detecting electrical signals produced by the heart, analyzing the signals for arrhythmia, and providing an appropriate therapy to terminate or reduce the arrhythmia. The pulse generator 501 is coupled to a cardiac lead system having sensing and therapy electrodes 550, 522 electrically coupled to the patient's heart. The cardiac lead system sensing and therapy electrodes 550, 522 may include one or more electrodes positioned in or around the heart as well as one or more electrodes positioned on the housing 590 or header of the pulse generator 501. In one arrangement, the electrodes used for sensing are also used for therapy delivery. In another arrangement, a set of therapy electrodes different from the sensing electrodes is used.

Cardiac signals sensed by sensing electrodes 550 of the cardiac lead system are coupled to an arrhythmia analysis unit 556 configured to identify cardiac arrhythmias. The arrhythmia analysis unit 556 may use information derived from a sleep state processor 552 to provide sleep state informed arrhythmia detection. If cardiac arrhythmia is detected, the therapy unit 542 may provide a number of therapies to treat the detected arrhythmia.

The cardiac therapy may include pacing therapy controlled to treat cardiac rhythms that are too slow. In this situation, the therapy unit 542 controls the delivery of periodic low energy pacing pulses to one or more heart chambers through pacing electrodes of the cardiac lead system 550. The pacing pulses ensure that the periodic contractions of the heart are maintained at a hemodynamically sufficient rate.

The cardiac therapy may also include therapy to terminate tachyarrhythmia, wherein the heart rhythm is too fast. The arrhythmia analysis unit 556 detects and treats episodes of tachyarrhythmia, including tachycardia and/or fibrillation. The arrhythmia analysis unit 556 recognizes cardiac rhythms consistent with various types of tachyarrhythmia. When tachyarrhythmia is identified, the therapy unit 522 may deliver high energy electrical stimulation to the heart through defibrillation electrodes of the cardiac lead system 550 to terminate the arrhythmia.

Implementation of an appropriate cardiac therapy may be augmented using autonomic balance information and sleep state classification determined by the sleep state processor 552 in accordance with embodiments of the invention. As previously discussed, neurohormonal activity and sleep state classification may be used to determine an optimal or more efficacious arrhythmia therapy. In one illustrative implementation, cardiac therapy may be triggered by signals from the sleep state processor 552 to prevent cardiac arrhythmia during proarrhythmic sleep periods. In another example, the lower rate limit of a bradycardia pacing regimen may be modified when the sleep state processor 552 indicates that the patient is asleep.

The sleep state processor 552 performs sleep state classification based on one or more signals, including autonomic balance information obtained from EGMs or other autonomic balance sensors 548. In the illustrative embodiment of FIG. 5, an autonomic balance sensor 548, for example, an EEG sensor used to calculate the LF/HF ratio, provides a signal to the sleep state processor 552. The autonomic balance sensor 548 need not be an independent or additional sensor, but may utilize one or more of the cardiac sensing electrodes 550 to determine or calculate neurohormonal information. Additionally, a signal responsive to the patient's activity may be used in combination with the autonomic balance information to augment sleep state classification. In the example implementation illustrated in FIG. 5, the patient activity signal is provided by an accelerometer 546.

The medical device 500 may optionally include components for performing respiratory system analysis 554 and delivering respiration therapy 520. In one embodiment, the patient's respiration patterns may be analyzed with knowledge of the patient's sleep state to determine an appropriate therapy to mitigate detected episodes of disordered breathing or to prevent the occurrence of sleep-disordered breathing.

A transthoracic impedance sensor 544 may be implemented to produce a signal representing the patient's respiration cycles. A respiration analysis unit 554 uses sleep state information provided by the sleep state processor 552 in analyzing the patient's respiration patterns to detect episodes of sleep-disordered breathing. Based on sleep state classification, respiration analysis, and, optionally, cardiac system analysis, respiration therapy may be delivered to the patient to mitigate or prevent respiratory disorders, including sleep apnea, hypopnea, or other forms of disordered breathing. Disordered breathing therapy may include, for example, CPAP therapy, nerve stimulation, or cardiac pacing. According to one embodiment, preventive respiratory therapy may be initiated if the sleep state classification processor indicates the patient is asleep, or upon detection of a particular sleep state.

Referring now to FIG. 6, the implantable device illustrated in FIG. 6 is an embodiment of a PIMD using autonomic balance information and patient activity information to classify sleep state and determine periods of cardiac vulnerability in accordance with the present invention. In this example, the implantable device includes a cardiac rhythm management device (CRM) 600 including an implantable pulse generator 605 electrically and physically coupled to an intracardiac lead system 610.

Portions of the intracardiac lead system 610 are inserted into the patient's heart 690. The intracardiac lead system 610 includes one or more electrodes configured to sense electrical cardiac activity of the heart, deliver electrical stimulation to the heart, sense the patient's transthoracic impedance, and/or sense other physiological parameters, e.g. cardiac chamber pressure or temperature. Portions of the housing 601 of the pulse generator 605 may optionally serve as a can electrode.

Communications circuitry is disposed within the housing 601 for facilitating communication between the pulse generator 605 and an external communication device, such as a portable or bed-side communication station, patient-carried/worn communication station, or external programmer, for example. The communications circuitry may also facilitate unidirectional or bidirectional communication with one or more implanted, external, cutaneous, or subcutaneous physiologic or non-physiologic sensors, patient-input devices and/or information systems.

The pulse generator 605 may optionally incorporate a motion detector 620 that may be used to sense patient activity as well as various respiration and cardiac related conditions. For example, the motion detector 620 may be optionally configured to sense snoring, activity level, and/or chest wall movements associated with respiratory effort, for example. The motion detector 620 may be implemented as an accelerometer positioned in or on the housing 601 of the pulse generator 605. If the motion sensor is implemented as an accelerometer, the motion sensor may also provide respiratory, e.g. rales, coughing, and cardiac, e.g. S1-S4 heart sounds, murmurs, and other acoustic information.

The lead system 610 and pulse generator 605 of the CRM 600 may incorporate one or more transthoracic impedance sensors that may be used to acquire the patient's respiration waveform, or other respiration-related information. The transthoracic impedance sensor may include, for example, one or more intracardiac electrodes 641, 642, 651-655, 663 positioned in one or more chambers of the heart 690. The intracardiac electrodes 641, 642, 651-655, 663 may be coupled to impedance drive/sense circuitry 630 positioned within the housing of the pulse generator 605.

In one implementation, impedance drive/sense circuitry 630 generates a current that flows through the tissue between an impedance drive electrode 651 and a can electrode on the housing 601 of the pulse generator 605. The voltage at an impedance sense electrode 652 relative to the can electrode changes as the patient's transthoracic impedance changes. The voltage signal developed between the impedance sense electrode 652 and the can electrode is detected by the impedance sense circuitry 630. Other locations and/or combinations of impedance sense and drive electrodes are also possible.

The voltage signal developed at the impedance sense electrode 652 is proportional to the patient's transthoracic impedance and represents the patient's respiration waveform. The transthoracic impedance increases during respiratory inspiration yielding a waveform with a positive slope. The transthoracic impedance decreases during respiratory expiration yielding a portion of the waveform having a negative slope. The peak-to-peak transition of the transthoracic impedance is proportional to the amount of air moved in one breath, denoted the tidal volume. The amount of air moved per minute is denoted the minute ventilation. A normal "at rest" respiration pattern, e.g., during non-REM sleep, includes regular, rhythmic inspiration-expiration cycles without substantial interruptions.

The lead system 610 may include one or more cardiac pace/sense electrodes 651-655 positioned in, on, or about one or more heart chambers for sensing electrical signals from the patient's heart 690 and/or delivering pacing pulses to the heart 690. The intracardiac sense/pace electrodes 651-655, such as those illustrated in FIG. 6, may be used to sense and/or pace one or more chambers of the heart, including the left ventricle, the right ventricle, the left atrium and/or the right atrium. The lead system 610 may include one or more defibrillation electrodes 641, 642 for delivering defibrillation/cardioversion shocks to the heart.

The pulse generator 605 may include circuitry for detecting cardiac arrhythmias and/or for controlling pacing or defibrillation therapy in the form of electrical stimulation pulses or shocks delivered to the heart through the lead system 610. The pulse generator 605 may also incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243; 6,360,127; 6,597,951; and US Patent Publication No. 2002/0143264, which are hereby incorporated herein by reference.

Figure 7:
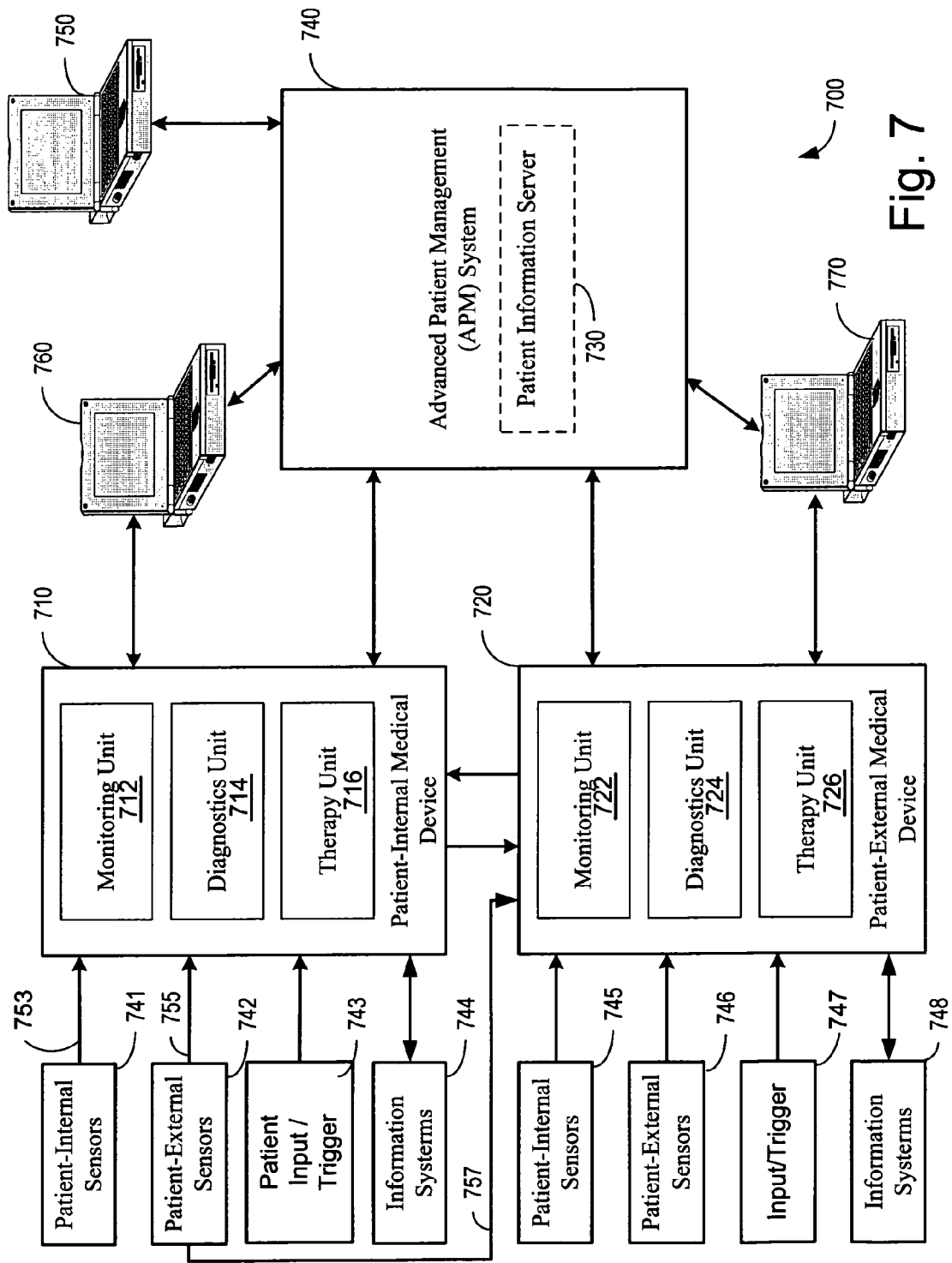
FIG. 7 is a block diagram of a medical system that may be used to implement system updating, coordinated patient monitoring, diagnosis, and/or therapy in accordance with embodiments of the present invention.

Referring now to FIG. 7, a PIMD of the present invention may be used within the structure of an advanced patient management (APM) system 700. The advanced patient management system 700 allows physicians to remotely and automatically monitor cardiac and respiratory functions, as well as other patient conditions. In one example, a PIMD implemented as a cardiac pacemaker, defibrillator, or resynchronization device may be equipped with various telecommunications and information technologies that enable real-time data collection, diagnosis, and treatment of the patient. Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

As is illustrated in FIG. 7, the medical system 700 may be used to implement coordinated patient measuring and/or monitoring, diagnosis, and/or therapy in accordance with embodiments of the invention. The medical system 700 may include, for example, one or more patient-internal medical devices 710, such as a PIMD, and one or more patient-external medical devices 720, such as a monitor or signal display device. Each of the patient-internal 710 and patient-external 720 medical devices may include one or more of a patient monitoring unit 712, 722, a diagnostics unit 714, 724, and/or a therapy unit 716, 726.

The patient-external medical device 720 performs monitoring, and/or diagnosis and/or therapy functions external to the patient (i.e., not invasively implanted within the patient's body). The patient-external medical device 720 may be positioned on the patient, near the patient, or in any location external to the patient.

The patient-internal and patient-external medical devices 710, 720 may be coupled to one or more sensors 741, 742, 745, 746, patient input/trigger devices 743, 747 and/or other information acquisition devices 744, 748. The sensors 741, 742, 745, 746, patient input/trigger devices 743, 747, and/or other information acquisition devices 744, 748 may be employed to detect conditions relevant to the monitoring, diagnostic, and/or therapeutic functions of the patient-internal and patient-external medical devices 710, 720.

The medical devices 710, 720 may each be coupled to one or more patient-internal sensors 741, 745 that are fully or partially implantable within the patient. The medical devices 710, 720 may also be coupled to patient-external sensors positioned on, near, or in a remote location with respect to the patient. The patient-internal and patient-external sensors are used to sense conditions, such as physiological or environmental conditions, that affect the patient.

The patient-internal sensors 741 may be coupled to the patient-internal medical device 710 through one or more internal leads 753. Still referring to FIG. 7, one or more patient-internal sensors 741 may be equipped with transceiver circuitry to support wireless communications between the one or more patient-internal sensors 741 and the patient-internal medical device 710 and/or the patient-external medical device 720.

The patient-external sensors 742 may be coupled to the patient-internal medical device 710 and/or the patient-external medical device 720 through one or more internal leads 755 or through wireless connections. Patient-external sensors 742 may communicate with the patient-internal medical device 710 wirelessly. Patient-external sensors 742 may be coupled to the patient-external medical device 720 through one or more internal leads 757 or through a wireless link.

In an embodiment of the present invention, the patient-external medical device 720 includes a visual display configured to concurrently display non-electrophysiological signals and EGM signals, including marked signals containing autonomic balance information. For example, the display may present the information visually. The patient-external medical device 720 may also, or alternately, provide signals to other components of the medical system 700 for presentation to a clinician, whether local to the patient or remote to the patient.

Referring still to FIG. 7, the medical devices 710, 720 may be connected to one or more information acquisition devices 744, 748, such as a database that stores information useful in connection with the monitoring, diagnostic, or therapy functions of the medical devices 710, 720. For example, one or more of the medical devices 710, 720 may be coupled through a network to a patient information server 730.

The input/trigger devices 743, 747 are used to allow the physician, clinician, and/or patient to manually trigger and/or transfer information to the medical devices 710, 720. The input/trigger devices 743, 747 may be particularly useful for inputting information concerning patient perceptions, such as a perceived cardiac event, how well the patient feels, and other information not automatically sensed or detected by the medical devices 710, 720. For example, the patient may trigger the input/trigger device 743 upon perceiving a cardiac event. The trigger may then initiate the recording of cardiac signals and/or other sensor signals in the patient-internal device 710. Later, a clinician may trigger the input/trigger device 747, initiating the transfer of the recorded cardiac and/or other signals from the patient-internal device 710 to the patient-external device 720 for display and diagnosis.

In one embodiment, the patient-internal medical device 710 and the patient-external medical device 720 may communicate through a wireless link between the medical devices 710, 720. For example, the patient-internal and patient-external devices 710, 720 may be coupled through a short-range radio link, such as Bluetooth, IEEE 802.11, and/or a proprietary wireless protocol. The communications link may facilitate unidirectional or bi-directional communication between the patient-internal 710 and patient-external 720 medical devices. Data and/or control signals may be transmitted between the patient-internal 710 and patient-external 720 medical devices to coordinate the functions of the medical devices 710, 720.

In another embodiment, patient data may be downloaded from one or more of the medical devices periodically or on command, and stored at the patient information server 730.

The physician and/or the patient may communicate with the medical devices and the patient information server 730, for example, to acquire patient data or to initiate, terminate or modify recording and/or therapy.

The data stored on the patient information server 730 may be accessible by the patient and the patient's physician through one or more terminals 750, e.g., remote computers located in the patient's home or the physician's office. The patient information server 730 may be used to communicate to one or more of the patient-internal and patient-external medical devices 710, 720 to provide remote control of the monitoring, diagnosis, and/or therapy functions of the medical devices 710, 720.

In one embodiment, the patient's physician may access patient data transmitted from the medical devices 710, 720 to the patient information server 730. After evaluation of the patient data, the patient's physician may communicate with one or more of the patient-internal or patient-external devices 710, 720 through an APM system 740 to initiate, terminate, or modify the monitoring, diagnostic, and/or therapy functions of the patient-internal and/or patient-external medical systems 710, 720.

In another embodiment, the patient-internal and patient-external medical devices 710, 720 may not communicate directly, but may communicate indirectly through the APM system 740. In this embodiment, the APM system 740 may operate as an intermediary between two or more of the medical devices 710, 720. For example, data and/or control information may be transferred from one of the medical devices 710, 720 to the APM system 740. The APM system 740 may transfer the data and/or control information to another of the medical devices 710, 720.

In one embodiment, the APM system 740 may communicate directly with the patient-internal and/or patient-external medical devices 710, 720. In another embodiment, the APM system 740 may communicate with the patient-internal and/or patient-external medical devices 710, 720 through medical device programmers 760, 770 respectively associated with each medical device 710, 720. As was stated previously, the patient-internal medical device 710 may take the form of an implantable PIMD.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method, comprising:
   acquiring a cardiac waveform from a patient using an implantable cardiac device provided in a patient;
   detecting one or more characteristics associated with autonomic balance of the patient; and
   using the one or more autonomic balance characteristics to evaluate one or more patient conditions, the one or more patient conditions comprising sleep onset.

2. The method of claim 1, wherein the one or more patient conditions comprise sleep stage.

3. The method of claim 1, wherein the one or more patient conditions comprise cardiac vulnerability over a predetermined duration.

4. The method of claim 3, wherein the predetermined duration is during patient sleep.

5. The method of claim 1, wherein the one or more patient conditions comprise sleep disordered breathing.

6. The method of claim 1, comprising:
   sensing a patient activity level; and
   further evaluating the patient's condition using the sensed patient activity level.

7. The method of claim 6, wherein further evaluating the patient's condition comprises determining a level of systemic stress.

8. The method of claim 1, wherein detecting the one or more characteristics associated with the autonomic balance comprises calculating an LF/HF ratio waveform and determining one or more morphological features of the LF/HF ratio waveform.

9. The method of claim 1, comprising generating a marked cardiac waveform using the cardiac waveform and one or more symbols indicating the one or more characteristics associated with the autonomic balance.

10. The method of claim 9, further comprising transmitting information about one or more of the cardiac waveform, the one or more characteristics associated with the autonomic balance, and the marked cardiac waveform to a patient-external device.

11. A cardiac system, comprising:
    a housing configured for implantation in a patient;
    a plurality of electrodes coupled to the housing and configured for sensing a cardiac waveform;
    a memory; and
    a controller provided in the housing and coupled to the memory and the plurality of electrodes, the controller configured to detect one or more characteristics associated with an autonomic balance of the patient, and use the one or more autonomic balance characteristics to detect patient sleep and evaluate a patient condition.

12. The system of claim 11, comprising a patient-external device, wherein the controller and the patient-external device are coupled to respective communication devices to facilitate wireless communication between the patient-external device and the controller.

13. The system of claim 11, wherein the controller is configured to classify the cardiac waveform as associated with one or more of sleep state, sleep stage, and sleep apnea.

14. The system of claim 11, comprising a lead coupled to the controller and configured for implantation in a patient, wherein one or more of the plurality of electrodes is supported by the lead.

15. A cardiac system, comprising:
    means for acquiring a cardiac waveform;
    means for detecting one or more characteristics associated with an autonomic balance of a patient; and
    means for detecting patient sleep and evaluating a patient condition using the one or more characteristics associated with the autonomic balance.

16. The system of claim 15, comprising means for determining a patient activity level using the transthoracic impedance.

17. The system of claim 15, comprising means for calculating an LF/HF ratio.

18. The system of claim 15, comprising means for generating a marked cardiac waveform using the cardiac waveform and one or more symbols indicating the one or more characteristics associated with the autonomic balance.

19. The system of claim 18, further comprising means for transmitting information about one or more of the cardiac waveform, the one or more characteristics associated with the patient autonomic balance, and the marked cardiac waveform to a patient-external device.

* * * * *

UNITED STATES PATENT AND TRADEMARK OFFICE
CERTIFICATE OF CORRECTION

| | | |
|---|---|---|
| PATENT NO. | : 7,899,519 B2 | Page 1 of 1 |
| APPLICATION NO. | : 11/168614 | |
| DATED | : March 1, 2011 | |
| INVENTOR(S) | : Carlson et al. | |

It is certified that error appears in the above-identified patent and that said Letters Patent is hereby corrected as shown below:

In the Title:

Title page, Item (54) and at Column 1, line 3: "IMPLATABLE" should read --IMPLANTABLE--.

In the Specification:

Col. 12, line 11: "tachyarrhymias" should read --tachyarrhythmias--.

Signed and Sealed this
Twenty-first Day of June, 2011

David J. Kappos
*Director of the United States Patent and Trademark Office*